United States Patent [19]

Dessau et al.

[11] Patent Number: 4,910,357
[45] Date of Patent: Mar. 20, 1990

[54] ALKYLATE UPGRADING

[75] Inventors: Ralph M. Dessau, Edison; Paul G. Rodewald, Rocky Hill, both of N.J.

[73] Assignee: Mobil Oil Corporation, New York, N.Y.

[21] Appl. No.: 210,952

[22] Filed: Jun. 24, 1988

[51] Int. Cl.$^4$ .................. C07C 6/08; C10G 35/085; C10G 35/095
[52] U.S. Cl. .................. 585/322; 585/331; 585/418; 585/419; 208/138
[58] Field of Search ............. 585/418, 419, 322, 331; 208/138

[56] References Cited

U.S. PATENT DOCUMENTS

| Re. 29,948 | 3/1979 | Dwyer et al. | 208/110 |
|---|---|---|---|
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 4,104,320 | 8/1978 | Bernard et al. | 260/673.5 |
| 4,300,015 | 11/1981 | Kirsch et al. | 585/722 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/166 |
| 4,652,360 | 3/1987 | Dessau | 585/419 |

FOREIGN PATENT DOCUMENTS

| 0107389 | 4/1984 | European Pat. Off. |
| 2033358 | 5/1980 | United Kingdom . |
| 2114150 | 8/1983 | United Kingdom . |

OTHER PUBLICATIONS

G. Wengui et al, "IR Study of Framework Vibrations and Surface Properties High Silica Zeolites", Zeolites, Elsevir Science, Amsterdam, 1985, p. 279.

Ione, Journal of Molecular Catalysis, 31, pp. 355–370 (1985).

Ione, "Structure and Reactivity of Modified Zeolites", Elsevir Science (1984), pp. 151–155.

Huagong, vol. 15, No. 7 (1986) (with translation).

*Primary Examiner*—Curtis R. Davis
*Attorney, Agent, or Firm*—Alexander J. McKillop; Charles J. Speciale; Marina V. Schneller

[57] ABSTRACT

A process selective for converting dimethylhexanes to aromatic analogs is described. Application of the exhibited selectivity of the process allows upgrading alkylate dimethylhexane(s) of low RON to produce higher RON analogs without affecting changes in other components of the alkylate. The catalysts preferred comprise platinum and non-acidic supports such as [Sn]ZSM-5 and [In]ZSM-5.

22 Claims, No Drawings

ALKYLATE UPGRADING

FIELD OF THE INVENTION

The invention relates to upgrading typical alkylates to increase the research octane number (RON) by preferentially converting the low octane components of the alkylate into aromatic components having research octane numbers greater than that of the low octane component. The catalytic conversion is effective in the presence of a catalyst comprising a strong dehydrogenation metal, such as platinum, in combination with a non-acidic microporous crystalline material characterized by an X-ray diffraction pattern of a zeolite having a constraint index of less than 12.

BACKGROUND OF THE INVENTION

Alkylate, as the term is used in the petroleum refining art, relates to a high octane product produced by the addition of an iso-paraffin, usually iso-butane, to one or more of the low molecular weight olefins, generally propylene or butylene, but also including amalene (pentene) or ethylene. The olefin source used to produce the alkylate is a biproduct of catalytic cracking. Generally, $C_3$ and $C_4$ olefins are produced in catalytic cracking. Isobutane is a product of hydrocracking processes.

Alkylation of isobutene with olefins was generally commercialized during World War II to provide a high octane component for aviation gasoline. It is now widely used as a source of high octane motor gasoline blending stock.

There are two major commercial alkylates processes, based on the acid catalyst used, HF or $H_2SO_4$. Both types of processes can be operated to give essentially the same yield and octane alkylate using butylene and/or propylene feed with iso-butane. The primary differences in process design are based on reactor engineering, to accommodate process requirements of either type of process. The HF units normally operate at about 80°–100° F. and can be controlled with water cooling. $H_2SO_4$ units require some form of refrigeration to control the temperature to below 50° F. Other acid catalysts have been employed for alkylation. Ethylene alkylation using aluminum chloride catalysts produces a very high clear octane gasoline component. However, the costs for ethylene and aluminum chloride make this process less economical than the HF and/or $H_2SO_4$ processes.

Isoparaffin-olefins alkylates, despite their high octane ratings, contain varying amounts of low octane components. Dimethylhexanes are prominent low octane components of those alkylates. The average RONs of the dimethylhexanes are well below 70, whereas, those of the trimethylpentanes are in the 100–110 RON range. The variance in the RON numbers for components of the alkylate are illustrated by the following table:

TABLE 1

| Components Contained in Isobutane HF Alkylates | | | | |
|---|---|---|---|---|
| Component | RON | i-Butene[a] | Butene-1[a] | Butene-2[a] |
| 2,3-Dimethylbutane | 103.5 | 1.5 | 0.6 | 2.5 vol % |
| 2,3-Dimethylpentane | 91.1 | 2.7 | 1.7 | 1.4 |
| 2,4-Dimethylpentane | 83.1 | 2.3 | 1.3 | 2.4 |
| 2,2,4-Trimethylpentane | 100.0 | 49.0 | 29.5 | 37.9 |
| 2,2,3-Trimethylpentane | 109.6 | 1.5 | 0.9 | 2.4 |
| 2,3,4-Trimethylpentane | 102.5 | 9.4 | 14.1 | 19.4 |
| 2,3,3-Trimethylpentane | 106.0 | 6.8 | 8.2 | 10.1 |
| 2,4-Dimethylhexane | 65.2 | 3.3 | 4.9 | 2.6 |

TABLE 1-continued

| Components Contained in Isobutane HF Alkylates | | | | |
|---|---|---|---|---|
| Component | RON | i-Butene[a] | Butene-1[a] | Butene-2[a] |
| 2,5-Dimethylhexane | 55.2 | 2.9 | 1.9 | 2.8 |
| 2,3-Dimethylhexane | 71.3 | 2.4 | 25.2 | 3.4 |

[a]Olefin used to prepare isobutane alkylate

SUMMARY OF THE INVENTION

The invention relates to upgrading alkylates containing dimethylhexanes, low octane components of alkylates, by selective aromatization of these components. In accordance with the invention, not only does that conversion occur; but also the trimethylpentane components of the alkylate, which are the high RON components of the alkylate, are unconverted, reflecting the low, if nonexistent, selectivity of the process for catalytic conversion of the trimethylpentane components of the alkylate.

DETAILED DESCRIPTION OF THE INVENTION

The dehydrocyclization of dimethylhexanes (including 2,5-, 2,4- and 2,3-dimethylhexanes), in accordance with the invention is undertaken by passing a mixture of dimethylhexanes and other components which are aliphatic compounds containing typically 4–9 carbon atoms over a catalyst comprising a strong dehydrogenation metal and a non-acidic support. The dimethylhexanes which have RONs between 55–71, in accordance with the invention, are converted to aromatics which have higher RONs than the dimethylhexanes. Moreover, when the dimethylhexanes are admixed with trimethylpentanes, those trimethylpentanes of high RON, ranging from 100–110 RON, remain unconverted, under those conditions under which the dimethylhexanes are converted to aromatics.

The catalytic conversion conditions for producing the aromatics from the dimethylhexanes include temperatures ranging from between about 400° to about 600° C., pressures ranging from about between 0 up to about 200 psig; and weight hourly space velocities (WHSV) ranging from about 0.1 up to about 10. Hydrogen or inert diluents such as nitrogen, or methane or nonaromatizable diluents such as propane, or $C_5$-paraffin fractions, or aromatics can also be co-fed with the source of dimethylhexanes to be converted to aromatics.

The catalysts employed in accordance with the invention comprise a strong dehydrogenation metal in combination with a non-acidic support. The dehydrogenation metal can comprise from 0.5 to 20 weight percent of the catalyst composition; preferably the dehydrogenation metal comprises from 0.1 to about 10 weight percent of the catalyst composition. The dehydrogenation metal can be any conventional dehydrogenation metal used in the art. Preferably the dehydrogenation metal is a platinum group metal. In embodiments described below, the dehydrogenation metal is platinum.

The non-acidic support component of the catalyst used in accordance with the invention is a crystalline microporous material, such as the zeolites, ALPOs or SAPOs. Non-acidic zeolite supports include microporous crystalline materials containing silicon and optionally aluminum. The acidity (or non-acidity) of zeolites can depend on the framework aluminum content and—

/or on the amount of compensating cations, such as Na+, K+, Cs+, etc. Decreasing acidity of zeolites can be effected by decreasing framework aluminum content. Compensating cations, such as alkali metal cations, exchanged for acidic protons in zeolites also renders the zeolites non-acidic. The most preferred zeolites used in the process of the invention are those which have been synthesized to contain indium, tin, thallium or lead in addition to the framework silicon. These are described in the Examples below.

Compositions used as catalysts in accordance with the invention do not exhibit any appreciable acid activity. These catalysts will meet the criteria of non-acidic catalysts described by Davis and Venuto, J. CATAL., Vol. 15, page 363 (1969). Alternatively, the non-acidic compositions will exhibit a pH of at least six when added to distilled deionized pH 7 water maintained under inert (such as argon) atmosphere; by an inert atmosphere in this context it means an atmosphere free of $CO_2$. Typically, in these tests 100 mg of catalysts is added to 30 ml. of distilled deionized water. Some compositions will exhibit a pH of at least 7.5.

The indium, tin, thallium or lead content of the crystalline materials can range from 0.01 to 20 weight percent. Practically, the indium, tin, thallium or lead content will range from 0.1 to 10 weight percent of the microporous crystalline silicate. The crystalline microporous materials are characterized by Si/Al ratios of at least 2. However, the silica:alumina ratio can be up to 1000 or even greater. In specific embodiments, the aluminum content of some of these materials is less than 0.1 weight percent. The crystalline microporous silicate materials containing tin, indium, thallium or lead can contain other elements including boron, iron, chromium and gallium. The content of these other elements in the microporous crystalline material can range from 0 to 10 weight percent.

The microporous crystalline materials can have the X-ray diffraction pattern which corresponds to a zeolite, SAPO, ALPO, etc. For example, indium compositions which can be used in accordance with the invention have been made, the crystal structure of which is that of ZSM-5, ZSM-11, ZSM-12, ZSM-23, ZSM-48, ZSM-50, zeolite beta, ZSM-20, SAPO-5 and ALPO-5. These are characterized by pore sizes up to about eight angstroms. The X-ray diffraction pattern and significant lines tables of these materials have been described in the U.S. Patent literature. In a preferred embodiment the pore size of the microporous crystalline silicate materials containing tin or indium ranges from 5 to about 8 angstroms.

When, as in embodiments herein, the non-acidic support exhibits an X-ray diffraction pattern of a zeolite, at least some of the dehydrogenation metal may be intra zeolitic, that is, some of that metal is within the pore structure of the crystal although some of that metal can be on the surface of the crystal. A test for determining whether, for example, Pt is intra zeolite or extra zeolitic in the case of ZSM-5 is reported by R. M. Dessau, J. CATAL., Vol. 89, page 520 (1984). The test is based on the selective hydrogenation of olefins.

The following Examples will illustrate the invention.

EXAMPLES

EXAMPLE 1

A 95 RON alkylate made from iso-butane and butene-2 (cis- and trans-) over a HF-BF3 graphite intercalate was passed over a non-acidic Pt/Sn-ZSM-5 catalyst at 538° C. in the absence of any carrier, 1 WHSV, and atmospheric pressure. The catalyst, containing 1.5 wt. % platinum; 2.7 wt. % tin; 0.63 wt. % Na and 72 ppm $Al_2O_3$, was formed as in Example 2 below.

The reaction was conducted in a downflow glass reactor containing 0.86 g Pt/Sn-ZSM-5. The product was collected in a cold trap maintained below −16° C. GC analyses were performed on a 30 m DB-1 capillary column, and GC-MS was used to confirm peak identifications.

The original composition of the alkylate mixture used is shown in Table 2. The bulk of the alkylate consisted of trimethylpentanes (58.4%), but it also containined 11.0% low octane dimethylhexanes. The research octane number of the alkylate was 95–96.

TABLE 2

| Composition of Alkylate Feed | |  |
|---|---|---|
| Component | Wt. % | |
| C4 i-Butane | 6.7 | |
| C5 i-Pentane | 1.1 | |
| C6 2,3-Dimethylbutane | 1.3 | |
| Methylpentanes | 0.6 | |
| C7 2,4-Dimethylpentane | 1.5 | |
| 2,3-Dimethylpentane | 0.8 | |
| C8 2,5-Dimethylhexane | 3.6 | |
| 2,4-Dimethylhexane | 4.1 | 11.0 |
| 2,3-Dimethylhexane | 3.3 | |
| 2,2,4-Trimethylpentane | 37.9 | |
| 2,2,3-Trimethylpentane | 0.6 | 58.4 |
| 2,3,4-Trimethylpentane | 13.9 | |
| 2,3,3-Trimethylpentane | 6.0 | |
| C9 2,2,4,4-Tetramethylpentane | 3.0 | |
| Other C9+ | 14.1 | |
| RON (clear) = 95–96 | | |

The aromatized alkylate product obtained by reaction over Pt/Sn-ZSM-5 was shown to contain 11.9% xylenes, in addition to lesser amounts of toluene and benzene (see Table 3). Greater than 90% conversion of the dimethylhexanes occurred, while 2,2,4-trimethylpentane conversion was about 10%. The measured RON of the product was 101.1, consistent with the selective conversion of low octane paraffins to aromatics.

TABLE 3

| Alkylate Upgrading Over Non-Acidic Pt/Sn-ZSM-5 | | |
|---|---|---|
| Selected Components | Alkylate | Product |
| C4− | 6.8% | 9.1% |
| Dimethylpentanes | 2.3 | 0.1 |
| Dimethylhexanes | 11.0 | less than 1 |
| 2,2,4-trimethylpentane | 37.9 | 33.0 |
| 2,3,4-trimethylpentane | 13.9 | 10.8 |
| Xylenes | 0 | 11.9 |
| Toluene | 0 | about 5 |
| Benzene | 0 | 3.7 |
| RON | 95–96 | 101.1 |

EXAMPLE 2

Tin containing ZSM-5 samples were synthesized by dissolving Sn(II)SO4 in deionized water and then adding NaOH. To this was added tetrapropylammonium bromide. The mixture was transferred to a 300 ml stainless steel autoclave and a low aluminum content silica gel (SPEX Ind.) was added with stirring. The resulting hydrogel was reacted at 160° C. for 5 days with stirring (400 rpm) before quenching. The resulting crystalline product was processed in the usual manner by filtering, washing and drying. X-ray diffraction analysis of the product zeolite showed it to be 100% crystalline ZSM-5.

B. Pt Metal Incorporation

The as-synthesized tin silicate was calcined first in nitrogen and then in air at 520° C. The calcined materials were ion-exchanged with aqueous Pt(NH$_3$)$_4$Cl$_2$ at room temperature at a pH of; typically, 15–20 mg per gram silicate was used. The platinum tetramine-containing silicates were then calcined in oxygen to 350° C. at 0.5° C./min.

EXAMPLE 3

[Sn]ZSM-5 was synthesized in the manner of Example 2 except that the SiO$_2$/Sn ratio was 150 and the Na$^+$/SiO$_2$ was 0.31. The crystalline ZSM-5 product contained 1.36% Sn, 0.0025% Al, 0.93% Na and 89.31% Ash.

EXAMPLE 4

Another [Sn]ZSM-5 was synthesized in that manner except that the SiO$_2$/Sn ratio was 50, the Na$^+$/SiO$_2$ was 0.38 and the synthesis time was 4 days.

EXAMPLE 5

Another [Sn]ZSM-5 was synthesized at a SiO$_2$/Sn ratio of 38, a Na$^+$/SiO$_2$ ratio of 0.40 and a synthesis time of 3 days.

EXAMPLE 6

Crystalline silicate products were produced containing indium and exhibiting characteristic X-ray diffraction patterns of structures corresponding to ZSM-5, ZSM-11, ZSM-12, ZSM-23, ZSM-48 and ZSM-50.

Table 4 compiles the composition ranges employed in the synthesis of a series of In/ZSM-5 products with widely varying indium content. Also shown in Table 4 is the synthesis of indium-containing silicates having X-ray pattern of ZSM-11, ZSM-12, ZSM-23, ZSM-48 and ZSM-50. The footnotes in Table 4 specify the SiO$_2$ sources and the organic directing agents employed in the synthesis.

TABLE 4

Crystallizations of Indium-Containing Zeolites
160° C.; Stirred 400 rpm

| Run No. | SiO$_2$/In$_2$O$_3$ | H$_2$O/SiO$_2$ | OH$^-$/SiO$_2$ | NA$^+$/SiO$_2$ | R/SiO$_2$ | Time, Days | Zeolite Product |
|---|---|---|---|---|---|---|---|
| 1[a] | 500 | 48 | 0.26 | 0.27 | 0.10[c] | 3 | ZSM-5 |
| 2[b] | 500 | 48 | 0.26 | 0.27 | 0.10[c] | 3 | ZSM-5 |
| 3[a] | 300 | 48 | 0.26 | 0.28 | 0.10[c] | 3 | ZSM-5 |
| 4[b] | 300 | 48 | 0.26 | 0.28 | 0.10[c] | 1 | ZSM-5 |
| 5[d] | 300 | 48 | 0.26 | 0.28 | 0.20[b] | 1 | ZSM-5 |
| 6[b] | 200 | 48 | 0.26 | 0.30 | 0.10[e] | 4 | ZSM-48 |
| 7[b] | 200 | 48 | 0.26 | 0.30 | 0.10[f] | 4 | ZSM-11 |
| 8[b] | 150 | 48 | 0.26 | 0.31 | 0.10[c] | 2 | ZSM-5 |
| 9[b] | 150 | 48 | 0.26 | 0.31 | 0.10[c] | 2 | ZSM-5 |
| 10[b] | 150 | 48 | 0.26 | 0.31 | 0.10[c] | 2 | ZSM-5 |
| 11[b] | 150 | 48 | 0.26 | 0.31 | 0.10[c] | 3 | ZSM-5 |
| 12[b] | 150 | 48 | 0.26 | 0.31 | 0.10[c] | 2 | ZSM-5 |
| 13[b] | 100 | 48 | 0.26 | 0.34 | 0.08[g] | 3 | ZSM-12 |
| 14[h] | 76 | 48 | 0.26 | 0.59 | 0.10[c] | 6 | ZSM-5 |
| 15[i] | 70 | 40 | 0.20 | 0.23 | 0.10[c] | 3 | ZSM-5 |
| 16[b] | 70 | 40 | 0.26 | 0.37 | 0.10[c] | 3 | ZSM-5 |
| 17[a] | 60 | 48 | 0.26 | 0.39 | 0.10[c] | 3 | ZSM-5 |
| 18[b] | 150 | 40 | 0.20 | 0.25 | 0.10[j] | 3 | ZSM-23 |
| 19[b] | 300 | 40 | 0.20 | 0.23 | 0.10[j] | 3 | ZSM-23 |
| 20[b] | 300 | 40 | 0.20 | 0.23 | 0.10[k] | 3 | ZSM-50 |

[a] Silica source is tetraethylorthosilicate (Et$_4$SiO$_4$)
[b] Silica source is SPEX Industries precipitated SiO$_2$
[c] R = TPA+
[d] Silica source is DeGussa fumed SiO$_2$

[e] R = DIQUAT-6 = (CH$_3$)$_3$N(CH$_2$)$_6$N(CH$_3$)$_3$
[f] R = TBA+

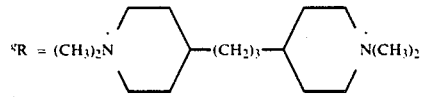

[g] R = (CH$_3$)$_2$N—⟨ring⟩—(CH$_2$)$_3$—⟨ring⟩—N(CH$_3$)$_2$

[h] Q-brand sodium silicate
[i] Silica source is kieselsaure precipitated SiO$_2$

[j] R = DIQUAT-7 = (CH$_3$)$_3$N(CH$_2$)$_7$N(CH$_3$)$_3$
[k] R = Dibenzyldimethylammonium ion Table 5 is a compilation of chemical analyses of some of the indium-containing products. These products vary in indium content from 0.36–5.20 wt% In. The formulas of the zeolite products are expressed in Table 5 as a ratio of oxides per mole of In$_2$O$_3$.

TABLE 5

Analyses of Some Indium-Containing Zeolitic Silicate Products

| Sample Run from No. | Weight Percent | | | | | | | Moles C / Moles N | Moles per Mole In$_2$O$_3$ | | | |
|---|---|---|---|---|---|---|---|---|---|---|---|---|
| | C | N | Na | In | SiO$_2$ | Al$_2$O$_3$ | Ash | | N$_2$O | Na$_2$O | Al$_2$O$_3$ | SiO$_2$ |
| 15 | 6.96 | 0.66 | 3.28 | 5.20 | 62.47 | 0.070 | 85.34 | 12.3 | 1.04 | 3.15 | 0.03 | 46 |
| 14 | 6.74 | 0.43 | 2.64 | 4.19 | 69.94 | 0.24 | 86.20 | 18.3 | 0.84 | 3.14 | 0.13 | 64 |

TABLE 5-continued

Analyses of Some Indium-Containing Zeolitic Silicate Products

| Sample Run from No. | Weight Percent | | | | | | | Moles C Moles N | Moles per Mole $In_2O_3$ | | | |
|---|---|---|---|---|---|---|---|---|---|---|---|---|
| | C | N | Na | In | $SiO_2$ | $Al_2O_3$ | Ash | | $N_2O$ | $Na_2O$ | $Al_2O_3$ | $SiO_2$ |
| 16 | 7.02 | 0.56 | 0.79 | 3.48 | 76.45 | 0.035 | 84.78 | 14.6 | 1.32 | 1.13 | 0.02 | 84 |
| 13 | 6.01 | 0.61 | 0.65 | 2.79 | 81.83 | 0.031 | 91.79 | 11.2 | 1.79 | 1.16 | 0.025 | 112 |
| 9 | 8.02 | 0.71 | 0.98 | 2.11 | 74.85 | 0.078 | 88.05 | 13.6 | 2.36 | 2.29 | 0.06 | 132 |
| 8 | 8.01 | 0.68 | 1.48 | 2.14 | 74.64 | 0.11 | 88.72 | 13.7 | 2.61 | 3.45 | 0.11 | 133 |
| 12 | 7.93 | 0.74 | 0.56 | 2.26 | 83.85 | 0.005 | 88.05 | 12.4 | 2.68 | 1.23 | 0.009 | 142 |
| 10 | 8.37 | 0.81 | 1.83 | 1.92 | 73.14 | 0.025 | 88.36 | 12.0 | 3.46 | 4.76 | 0.03 | 146 |
| 11 | 8.22 | 0.62 | 0.54 | 1.49 | 82.14 | 0.031 | 85.96 | 15.5 | 3.41 | 1.81 | 0.05 | 211 |
| 6 | 4.58 | 0.79 | 0.48 | 1.46 | 86.70 | 0.029 | 91.86 | 6.7 | 4.44 | 1.64 | 0.045 | 227 |
| 7 | 8.66 | 0.51 | 0.44 | 0.96 | 82.29 | 0.013 | 89.43 | 19.8 | 4.36 | 2.29 | 0.045 | 328 |
| 2 | 8.12 | 0.69 | 0.40 | 0.36 | 78.05 | 0.083 | 85.69 | 13.7 | 15.7 | 5.55 | 0.52 | 830 |

EXAMPLE 7

The In/ZSM-5 of that run No. 12 was prepared as follows:

The source of the indium can be incorporated into the zeolitic silicate synthesis reaction mixture as a partial, or preferably as a complete substitute for sources of alumina (or boron) conventially used in zeolite synthesis. In the embodiments described below the crystalline indium containing silicates were synthesized from crystallization reaction mixtures which contained no deliberately added sources of $Al_2O_3$.

A commercial silica gel (SPEX Ind.) with very low aluminum contamination was employed in the synthesis of In-ZSM-5. First, 0.85 g $In(NO_3)_3$ and 2.66 g NaOH pellets were dissolved in 180.2 g de-ionized water, then 5.64 g tetrapropylammonium bromide (TPABr) was dissolved in this basic solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

| | |
|---|---|
| $SiO_2/In_2O_3$ | 150 |
| $H_2O/SiO_2$ | 48 |
| $OH^-/SiO_2$ | 0.26 |
| $Na^+/SiO_2$ | 0.31 |
| $TPA^+/SiO_2$ | 0.10 |

The hydrogel was reacted at 160° C. for 2 days at a stirring rate of 400 rpm before quenching. The resultant crystalline product was filtered, washed, and dried. X-ray powder diffraction analysis showed the product to be 100% crystalline ZSM-5, when compared to the diffraction pattern of a conventional ZSM-5. Elemental analysis of the ZSM-5 product gave: C=7.93 wgt %, N=0.74%, Na=0.56%, In=2.26%, Al 0.005%, $SiO_2$=83.85%, Ash=88.05%.

These results expressed in mole ratios were: C/N=12.5; Moles/mole $In_2O_3$: $N_2O$=2.68, $Na_2O$=1.23, $Al_2O_3$=0.009, $SiO_2$=142.

Platinum incorporation was undertaken as follows: The as-synthesized zeolite was heated in nitrogen to 520° C. at 1° C./min and held there for 6 hours. It was then calcined in air in a similar manner. The calcined zeolite analyzed for 41.05% Si, 2.21% In (Si/In2=152), and 120 ppm Al, and sorbed 10.4% n-hexane at 90° C. The calcined zeolite (3 g) was stirred in a solution of 150 mg $Pt(NH_3)_4Cl_2$ in 100 ml water at room temperature overnight. After being washed, filtered and dried, the ion-exchanged zeolite was found to contain 0.41 meq $NH_3/g$ ash, which is equivalent to 1.89% Pt on sample. The platinum tetramine zeolite was then calcined in oxygen to 350° C. at 0.5° C./min and held there for 1 hour. Elemental analysis indicated the presence of 1.85% Pt on the final catalyst.

At very high hexane conversions (99%), benzene was formed in over 94% yield. Similarly, n-heptane yielded 96% toluene. Similarly, n-heptane yielded 96% toluene. Consistent with the non-acidic nature of this platinum catalyst, n-octane yielded predominantly ethylbenzene and ortho-xylene, 2-methylheptane produced mostly meta-xylene, and 3-methylheptane formed mainly ethylbenzene, para-, and ortho-xylene.

EXAMPLE 8

In EXAMPLE 6, zeolitic silicate was made using $In(NO_3)_3$ in the crystallization reaction mixture. In the Example below, indium was incorporated post-synthesis; in a subsequent step platinum was ion-exchanged onto the zeolite.

In this example, a high silica/alumina (10,000) ZSM-11 was calcined in nitrogen and then in air at 538° C. $InCl_3$ vapors were passed through the zeolite in a stream of nitrogen, while it was heated to 500° C. at 10° C./min. The zeolite was maintained at 500° C. for 1.5 hours. After cooling, the catalyst was added to 200 ml 1M $NH_4Cl$ adjusted to pH 9.5 with $NH_4OH$. The mixture was stirred for 20 minutes at room temperature, and then filtered. The zeolite was then reexchanged for 3 hours with 1M $NH_4Cl$ adjusted to pH 7.6. Thermogravimetric analysis indicated the presence of 0.325 meq/g ammonium ion in the zeolite.

Platinum was incorporated by ion exchange with $Pt(NH_3)_4Cl_2$ at room temperature. The platinum zeolite was then calcined in oxygen to 350° C. at 0.5° C./min.

Under aromatization conditions, the catalyst effected aromatization of n-heptane to toluene in high yield. At about 500° C. (up to about 538° C.) and 30 torr heptane in nitrogen, toluene was formed in 94% selectivity at a conversion level of greater than 90%.

EXAMPLE 9

The ZSM-5-type borosilicate was synthesized at 170° C. from a mixture of 12.4 high purity silica (SPEX), 105 g 20% TEA hydroxide, and 0.8 g boric acid. The as-synthesized zeolite was then calcined in nitrogen and then in air at 520° C. The calcined zeolite contained 41.39% Si, 0.015% Al, and 0.44% B.

Two grams of the calcined borosilicate was impregnated with 135 mg $In(NO_3)_3$, and calcined in air at 500° C. for 2 hours. 1.8 g of this material was then ion-exchanged with 28 mg $Pt(NH_3)_4Cl_2$ in 100 ml water at room temperature. TGA analysis in hydrogen indicated the presence of 0.18 meq N/g equivalent to 0.87% Pt.

The platinum-exchanged zeolite was then calcined in oxygen to 350° C. at 0.5° C./min.

The catalyst activity of the foregoing composition was examined. The "non-acidic" nature of the catalyst was confirmed by its ability to aromatize n-heptane to toluene in high yield. At 500° C. and 30 torr heptane in nitrogen, toluene was formed in 95% yield. Furthermore, the small amounts of both methane and propane produced were exceeded by the ethane formed, indicative of the low hydrogenolysis and acid activity of the catalyst.

| % Conversion | % C1 | % C2 | % Benzene | % Toluene (Selectivity) |
|---|---|---|---|---|
| 96 | 0.4 | 0.6 | 1.3 | 92 (96%) |
| 99 | 0.5 | 1.0 | 1.5 | 95 (96%) |

EXAMPLE 10

Indium-containing zeolite ZSM-20 was synthesized by the following procedure:

12.75 grams of sodium aluminate (NaAlO$_2$) and 6.02 grams indium nitrate were dissolved in 57.96 grams of deionized water. After the solid ingredients dissolved, 484.1 ml of 2.88N tetraethylammonium hydroxide (TEAOH) was added to the solution. The resulting solution was now stirred into 312.5 grams of tetraethylorthosilicate. This solution was kept stirring for one hour until the hydrolysis reaction was complete. The resulting hydrogel was now transferred to a one-liter polypropylene bottle.

The polypropylene bottle was loosely capped and placed into a steambox (100° C.) to promote the crystallization of the zeolite. The next morning the bottle was removed from the steambox and the bottle cap was now closed tightly. The bottle was shaken vigorously, then replaced into the steambox. The reaction mixture for the initial hydrogel formed for the synthesis of the indium-containing ZSM-20 can be described by the following set of mole ratios:

| | |
|---|---|
| SiO$_2$/In$_2$O$_3$ | 150 |
| H$_2$O/SiO$_2$ | 10 |
| OH$^-$/SiO$_2$ | 0.9 |
| Na$^+$/SiO$_2$ | 0.09 |
| TEA$^+$/SiO$_2$ | 0.93 |
| SiO$_2$/Al$_2$O$_3$ | 30 |

Samples of the solid product were removed daily from the polypropylene bottle for X-ray diffraction (XRD) analysis to determine the product crystallinity. XRD analysis showed that the ZSM-20 crystallization was complete in 14 days. The polypropylene bottle was removed from the steambox, and the solid product was filtered on a Buchner funnel. After filtration, the product zeolite was boiled in de-ionized water and again filtered and dried under an infrared heat lamp. After drying, a sample of the product was submitted for XRD and chemical analysis. XRD analysis showed the product to be zeolite ZSM-20. The chemical analysis for the indium-containing ZSM-20 was:

| | | Weight Percent | | | | |
|---|---|---|---|---|---|---|
| C | N | Na | In | SiO$_2$ | Al$_2$O$_3$ | Ash |
| 10.0 | 1.2 | 3.0 | 3.08 | 58.5 | 11.4 | 75.1 | which gives:

| | Moles per Mole In$_2$O$_3$ |
|---|---|
| Moles C | N$_2$O:Na$_2$O:Al$_2$O$_3$:SiO$_2$ |
| Moles N 9.7 | 3.19:4.86:8.33:72.7 |

EXAMPLE 11

Indium-containing zeolite Beta was synthesized in the following manner:

5.95 grams of sodium aluminate and 4.68 grams of indium nitrate were dissolved in 85.14 grams of de-ionized water. After the salts dissolved, 105.0 ml of 3.1N TEAOH was added to the solution. The resulting solution was transferred to a 300 ml stainless-steel autoclave.

Now 46.67 grams of solid silica gel (SPEX Industries) was pored into the autoclave, the autoclave was sealed and stirring and heating begun immediately. The reaction was carried out at 160° C. with stirring (400 rpm).

The initial reaction mixture for the synthesis of indium-containing zeolite Beta can be described by the mole ratios:

| | |
|---|---|
| SiO$_2$/In$_2$O$_3$ | 90 |
| H$_2$O/SiO$_2$ | 12 |
| OH$^-$/SiO$_2$ | 0.40 |
| Na$^+$/SiO$_2$ | 0.09 |
| TEA$^+$/SiO$_2$ | 0.46 |
| SiO$_2$/Al$_2$O$_3$ | 30 |

After 4 days the autoclave was quenched in a water plus ice bath to terminate the reaction. The solid product was filtered, boiled in water and again filtered. XRD analysis showed the crystalline product to be zeolite Beta. Chemical analysis of the indium-containing zeolite Beta product gave the following results:

| | | Weight Percent | | | | |
|---|---|---|---|---|---|---|
| C | N | Na | In | SiO$_2$ | Al$_2$O$_3$ | Ash |
| 10.84 | 1.71 | 1.4 | 2.5 | 69.8 | 4.2 | 79.92 | which gives:

| | Moles per Mole In$_2$O$_3$ |
|---|---|
| Moles C | N$_2$O:Na$_2$O:Al$_2$O$_3$:SiO$_2$ |
| Moles N 7.4 | 5.61  2.79  3.78  62.8 |

EXAMPLE 12

Indium-containing crystalline aluminophosphate molecular sieve ALPO-5 was synthesized as follows:

23.1 grams of concentrated phosphoric acid (86.3% H$_3$PO$_4$) was diluted with 30.0 grams of de-ionized water. Now 10.0 grams of Kaiser alumina was stirred into this acid solution and the mixture was digested for 45 minutes at 90° C. with continuous stirring. After the digestion period a solution containing 1.18 grams of indium nitrate dissolved in 41.0 grams of de-ionized water was stirred into the gel. Finally, 37.0 grams of 40% wt. TEAOH solution was stirred into the gel and stirring continued until a uniform gel was produced.

This gel was now transferred to a 300 ml stainless-steel autoclave. The resulting reaction mixture hydrogel can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $TEA^+/Al_2O_3$ | 1.0 |

The autoclave was sealed and heated and stirring begun immediately. The reaction was carried out at 160° C. with stirring (400 rpm).

After 4 days the autoclave was quenched in water-+ice bath to terminate the crystallization. The solid product was filtered, boiled in water and filtered again. After drying the product, XRD analysis showed the material to be crystalline aluminophosphate designated by Union Carbide as ALPO-5. Chemical analysis of the indium-containing ALPO-5 gave:

| Weight Percent | | | | | | |
|---|---|---|---|---|---|---|
| C | N | Na | P | Al | In | Ash |
| 6.66 | 0.84 | 0.48 | 21.05 | 16.01 | 1.44 | 89.45 | which gives:

| | Moles per Mole $In_2O_3$ |
|---|---|
| Moles C | $N_2O:Na_2:P_2O_5:Al_2O_3$ |
| Moles N 9.2 | 4.78  1.66  54.2  47.3 |

EXAMPLE 13

Indium-containing crystalline silicoaluminophosphate molecular sieve SAPO-5 was synthesized in a manner analogous to EXAMPLE 7:

46.2 grams of concentrated phosphoric acid (86.3% $H_3PO_4$) was first diluted with 60.0 grams of de-ionized water then 20.0 grams of Kaiser alumina was added to the solution. This mixture was now digested on a hot plate at 90° C. for 45 minutes, with continuous stirring. At the end of the digestion period, a solution containing 2.36 grams of indium nitrate dissolved in 82.0 grams of de-ionized water was stirred into the gel. Next 74.0 grams of 40% wt TEAOH solution was stirred into the gel. This mixture was now stirred at room temperature until a uniform hydrogel was produced. The resulting hydrogel was transferred to a one-liter stainless-steel autoclave. Before sealing the autoclave, 2.04 grams of tetraethylorthosilicate was transferred to the autoclave. The autoclave was then sealed and heating and stirring was begun immediately. The resulting reaction mixture can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $SiO_2/Al_2O_3$ | 0.10 |
| $TEA^+/Al_2O_3$ | 1.0 |

The crystallization of the indium-containing SAPO was carried out at 150° C. with stirring (400 rpm).

At the end of 4 days the autoclave was quenched in a water+ice bath to terminate the crystallization. The solid product was filtered, boiled in water, and re-filtered. After drying under a heat lamp, XRD analysis showed that the reflection lines for the product correspond to silicoaluminophosphate SAPO-5, a Union Carbide designation for this material.

Chemical analysis of the indium-containing SAPO-5 gave:

| Weight Percent | | | | | | | |
|---|---|---|---|---|---|---|---|
| C | N | Na | P | Al | In | Si | Ash |
| 6.32 | 0.60 | 0.48 | 19.88 | 15.71 | 1.45 | 0.66 | 85.00 | which gave

| | Moles per Mole $In_2O_3$ |
|---|---|
| Moles C | $N_2O:Na_2O:P_2O_5:Al_2O_3:SiO_2$ |
| Moles N 12.3 | 3.39  1.65  50.8  46.1  3.7 |

EXAMPLE 14

Platinum incorporation into the indium-containing silicate of ZSM-5 structure was carried out by direct addition of a platinum compound to the zeolite synthesis reaction mixture as follows:

A solution was prepared by dissolving 2.00 grams of indium nitrate and 13.07 grams of NaOH pellets in 710.28 grams of de-ionized water. After the solids dissolved, 26.6 grams of tetrapropylammonium bromide (TPABr) was dissolved in the solution. Finally 1.29 grams of platinum tetraaminenitrate $[Pt(NH_3)_4(NO_3)_2]$ was dissolved in the solution, and the solution was transferred to a one-liter stainless-steel autoclave. Before sealing the autoclave, 66.67 grams of commercial silica gel (SPEX Industries) was poured into the autoclave. The autoclave was then sealed and heating and stirring was begun immediately. The reaction mixture hydrogel can be described by the following mole ratios:

| | |
|---|---|
| $SiO_2/In_2O_3$ | 300 |
| $H_2O/SiO_2$ | 40 |
| $OH^-/SiO_2$ | 0.30 |
| $Na^+/SiO_2$ | 0.33 |
| $TPA^+/SiO_2$ | 0.10 |
| $SiO_2/Pt$ | 300 |

The crystallization was carried out at 170° C. with stirring (400 rpm).

After 4 days the autoclave was quenched in a water-+ice bath to terminate the crystallization. In the usual manner the solid product was filtered, boiled in water, and finally filtered again before drying under a heat lamp. XRD analysis of the solid product showed the material to be crystalline zeolite ZSM-5.

Chemical analysis of the indium-containing ZSM-5 product gave:

| Weight Percent | | | | | | | | |
|---|---|---|---|---|---|---|---|---|
| C | N | Na | In | Pt | $SiO_2$ | $Al_2O_3$ | Ash |
| 8.27 | 0.74 | 1.3 | 1.1 | 0.52 | 82.7 | 0.0265 | 85.05 | which gave:

|  | Moles per Mole In$_2$O$_3$ |
|---|---|
| Moles C | N$_2$O:Na$_2$O:Al$_2$O$_3$:SiO$_2$:Pt |
| Moles N | 5.52  5.90  0.05  288  0.55 |
| 13.1 | |

EXAMPLE 15

A boron-containing zeolite beta was synthesized and then calcined to remove the organic template, by heating first in N$_2$ 25°–530° at 10/min and held 6 hrs. then in air in N$_2$ 25°–530° at 10/min. and held 6 hours.

25 g of the calcined zeolite was ion-exchanged with 750 mg Pt(NH$_3$)$_4$ Cl$_2$ in 400 ml H$_2$O at room temperature overnight. The dried material was then calcined in flowing oxygen (100 cc/min.) 25°–350° at ½°/min. and held 1 hour.

10 g of the calcined Pt-containing zeolite was then treated with 0.9 g In(NO$_3$)$_3$ H$_2$O in 200 ml H$_2$O at room temperature overnight.

The zeolite was filtered and washed.

The In-containing Pt/zeolite was added to 150 ml H$_2$O and titrated to pH 9.0 with 0.5 MCsOH (1½ hrs). The material was filtered, washed, and dried. The final product contained 0.76% Pt, 11% Cs, 1.1% In, and 0.08% B.

EXAMPLE 16

The synthesis of a binary oxide zeolite having the structure of ZSM-5 was carried out in the two-phase system as in Ser. No. 878,555 filed June 26, 1986. The aqueous phase of the two-phase system comprised 2.8 g In(NO$_3$)$_3$xH$_2$O dissolved in 35 g water to which was added 63 g TPAOH (40% in H$_2$O). Constituting the organic phase was 77.0 g Si(OCH$_3$)$_4$ dissolved in 35 g of 1-hexanol. The mixture was nucleated at 180° C. for 24 hours and crystallized at 200° C. for 144 hours. The final product was filtered and washed. The X-ray diffraction pattern of the dried material proved it to be well-crystallized ZSM-5.

The sample was ammonium-exchanged (1M NH$_4$Cl, twice, 60° C, 20 ml/g zeolite) and calcined. The chemical composition of the ash of a 1000° C. calcined sample was 79.3 wt. % SiO$_2$ and 1.5 wt. % In$_2$O$_3$. The ash residue also contained a small quantity, i.e. 85 ppm, of aluminum.

Temperature-programmed desorption of ammonia indicated an exchange capacity of 0.09 meg/q for the product of this example. The Si/In ratio from TPAD was 190.5. The sample had an Alpha Value of 1.0

The particle size of the product from this example was about 0.2 microns. The particles were made of pure single crystals with almost cubic appearance.

EXAMPLE 17

The synthesis of Example 16 was repeated, except that the mixture contained 3.6 g In(NO$_3$)$_3$.xH$_2$O in the aqueous phase. The product material was filtered and dried. It had the same characteristic ZSM-5 X-ray lines as the product of Example 11. The material was calcined and ammonium-exchanged as described in Example 11. The chemical composition of the ash of a 1000° C. calcined sample was 78.2 wt. % SiO$_2$ and 3.1 wt. % In$_2$O$_3$. The ash residue also contained a small quantity, i.e. 180 ppm, of aluminum.

Temperature-programmed desorption of ammonia indicated an exchange capacity of 0.21 meq/g for the product of this example. The Si/In ratio from TPAD was 77.9. The sample had an Alpha Value of 2.5.

The particle size of the product from this example was about 0.2 microns. The particles were made of crystals with almost cubic appearance. There were no impurities present.

EXAMPLES 18–22

The synthesis of Example 16 was repeated, except that the mixtures contained varying amounts of In(-NO$_3$)$_3$.xH$_2$O. Five preparations were made, with the following compositions:

| Example | 18 | 19 | 20 | 21 | 22 |
|---|---|---|---|---|---|
| Aqueous Phase (g) | | | | | |
| H$_2$O | 40.0 | 40.0 | 35.0 | 40.0 | 40.0 |
| In(NO$_3$)$_3$ × 3H$_2$O | 0.9 | 7.2 | 1.8 | 1.8 | 3.6 |
| TPAOH, 40% | 63.0 | 63.0 | 63.0 | 63.0 | 63.0 |
| Organic Phase (g) | | | | | |
| 1-Hexanol | 60.0 | 60.0 | 35.0 | 60.0 | 60.0 |
| Si(OCH$_3$)$_4$ | 77.0 | 77.0 | 77.0 | 77.0 | 77.0 |

The product materials were filtered and dried. They had the same characteristic X-ray lines as ZSM-5. The materials were calcined and ammonium-exchanged as in Example 16. Their properties were as follows:

| EXAMPLE | 18 | 19 | 20 | 21 | 22 |
|---|---|---|---|---|---|
| SiO$_2$, wt. % | 84.0 | 77.5 | 80.5 | 76.7 | 82.5 |
| In$_2$O$_3$, wt. % | 0.67 | 5.1 | 1.58 | 1.31 | 2.92 |
| Al, ppm | 105 | 65 | 130 | 85 | 60 |
| Exchange Capacity, meq/g | 0.09 | 0.17 | 0.17 | 0.12 | 0.21 |
| Si/In (from TPAD) | 193 | 99 | 95 | 138 | 77 |
| Alpha Value | 1.5 | 1.6 | 1.0 | 1.0 | n.d. |
| Particle size | 2000A | 1 micr | 2000A | 2000A | 2000A |

EXAMPLE 23

Thallium ZSM-5 silicate synthesis was undertaken as follows: A solution was prepared by dissolving 0.85 g TlNO$_3$ in 170.6 g deionized water and then by adding 2.05 g NaOH pellets. After all the base had dissolved, 6.38 g tetrapropylammonium bromide (TPABr) was added. The resulting solution was transferred to a 300 ml stainless steel autoclave and 16.0 g of silica gel (SPEX Ind.) was stirred into the solution. The hydrogel produced can be described by the following mole ratios:

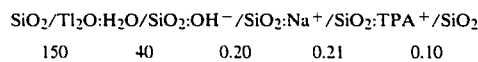

SiO$_2$/Tl$_2$O:H$_2$O/SiO$_2$:OH$^-$/SiO$_2$:Na$^+$/SiO$_2$:TPA$^+$/SiO$_2$
150    40    0.20    0.21    0.10

The hydrogel was heated in the autoclave for 4 days at 160° C., with stirring at 400 rpm. The product was filtered, washed and dried. X-ray diffraction analysis indicated it to be 100% crystalline ZSM-5.

Elemental analysis indicated the presence of 8.26% C., 1.88% H, 0.74% N, 0.34% Na, 4.33% Tl, 80.65% SiO$_2$, and 0.0095% Al in the ZSM-5 product.

EXAMPLE 24

Catalyst preparation was undertaken as follows: The as-synthesized thallium silicate was calcined, first in nitrogen and then in air, at 520° C. The calcined zeolite contained 2.43% Tl, 38 ppm Al, and 43.15% Si.

Platinum was incorporated by ion exchange with Pt(NH$_3$)$_4$Cl$_2$ (15 mg/g zeolite) at room temperature. TGA ammonia titration in hydrogen indicated the presence of 0.67% Pt. The platinum-containing zeolite was then calcined in oxygen to 350° C. where it was maintained for one hour at 0.5° C./min.

EXAMPLE 25

The "non-acidic" nature of the catalyst of Example 24 was confirmed by its ability to aromatize n-heptane to toluene in high yield. At 538° C. and 30 torr heptane in nitrogen, toluene was formed in 83–88% selectivity at a conversion of 99+%. Total yield of benzene plus toluene was greater than 90%.

EXAMPLE 26

The above catalyst of Example 24 was used to study the reforming of a hydrotreated Arab light naphtha, b.p. 180°–250° F. The reaction was run at 538° C. at atmospheric pressure at 1.8 WHSV and a N$_2$/HC ratio of 2.2. The results obtained are shown below:

|  | Feed | Product | % Converted |
|---|---|---|---|
| C$_1$–C$_4$ | 0 | 0.4 |  |
| Methylpentanes | 16.5 | 11.6 | 30% |
| n-Hexane | 24.2 | 12.2 | 50% |
| Methylhexanes | 15.6 | 11.8 | 24% |
| n-Heptane | 17.1 | 7.2 | 58% |
| Benzene | 2.1 | 14.0 |  |
| Toluene | 3.2 | 11.5 |  |

Preliminary screening of the thallium-modified non-acidic Pt/ZSM-5 catalyst described above for the reforming of a hydrotreated Arab light naphtha, b.p. 180°–250° F., indicated highly selective aromatics formation together with very low C$_1$–C$_4$ gas production. At 538° C., atmospheric pressure, 1.8 WHSV, and a N$_2$:HC ratio of 2.2, preferential conversion of the normal paraffins to benzene and toluene was observed, as shown above.

EXAMPLE 27

Lead-containing ZSM-5 was synthesized. A solution A was prepared by dissolving 3.31 g Pb(NO$_3$)$_2$ in 338.8 g de-ionized water. A solution B was prepared by dissolving 12.4 g NaOH in 300 g de-ionized water. 23.94 g TPA bromide was then dissolved in solution B, which was then poured into solution A. 60.0 g silica gel (SPEX Ind.) was placed in a 1-liter stainless steel autoclave. The solution was now transferred to the autoclave, and the mixture was stirred for two minutes before sealing the autoclave. Stirring and heating were begun immediately. The composition of the hydrogel formed is described by the following mole ratios:

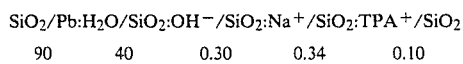

SiO$_2$/Pb:H$_2$O/SiO$_2$:OH$^-$/SiO$_2$:Na$^+$/SiO$_2$:TPA$^+$/SiO$_2$
90   40   0.30   0.34   0.10

The zeolite crystallization was carried out at 160° C. with stirring at 400 rpm for 4 days. The product ZSM-5 analyzed for 7.96% C, 0.7% N, 0.97% Na, 4.0% Pb, 86.48% ash, and 235 ppm Al$_2$O$_3$. Platinum incorporation was similar to that in Example 2.

EXAMPLES 28–35

The preparation of the borosilicate ZSM-5 has been described. High silica:alumina ZSM-5 samples containing the elements: chromium, titanium, scandium, nickel, gold, germanium, and zirconium were synthesized in a manner analogous to that used to prepare Tl-ZSM-5, described above. The synthesis conditions are show in in Table 6 below:

TABLE 6

Synthesis of Metal-Containing ZSM-5

| Example No. | Metal (M) Salt | Mixture Composition (Mole Ratio) | | | | | Time Days |
|---|---|---|---|---|---|---|---|
| | | SiO$_2$/M | H$_2$O/SiO$_2$ | OH$^-$/SiO$_2$ | Na$^+$/SiO$_2$ | TPA$^+$/SiO$_2$ | |
| 28 | Pb(NO$_3$)$_2$ | 90 | 40 | 0.30 | 0.34 | 0.10 | 4 |
| 29 | CrCl$_3$.6H$_2$O | 75 | 40 | 0.30 | 0.35 | 0.10 | 3 |
| 30 | TiCl$_4$ | 150 | 40 | 0.30 | 0.33 | 0.10 | 5 |
| 31 | Sc(NO$_3$)$_3$.4H$_2$O | 75 | 40 | 0.20 | 0.21 | 0.10 | 4 |
| 32 | Ni(NO$_3$)$_3$.6H$_2$O | 75 | 40 | 0.30 | 0.27 | 0.10 | 3 |
| 33 | Au(OH)$_3$ | 75 | 40 | 0.30 | 0.35 | 0.10 | 3 |
| 34 | GeCl$_4$ | 75 | 40 | 0.20 | 0.25 | 0.10 | 5 |
| 35 | Zr(NO$_3$)$_4$ | 75 | 48 | 0.26 | 0.31 | 0.10 | 3 |

(all syntheses used SPEX silica, temp = 160° C.), stirred

The synthesized zeolites all contained less than 0.06% Al and more than 0.4% Na. The final platinum-containing catalysts contained 0.57–0.80% Pt.

EXAMPLE 36

The apparent "alpha activity" of the non-acidic platinum containing zeolites was measured using the standard alpha apparatus in either helium or hydrogen over a period of 1–3 hours. The relative hexane conversion activities of the various Pt/ZSM-5 catalysts are shown in Table 7 below:

TABLE 7

Relative Hexane Conversion Activities for Various Pt/ZSM-5 Catalysts

| Catalyst | % Pt | % M | Activity$^{(a)}$ |
|---|---|---|---|
| hi Si | 0.6 | — | 746 |
| Sn | 1.5 | 2.7 | 1013 |
| In | 0.9 | 2.5 | 320 |
| Tl | 0.7 | 4.5 | 94 |
| Pb | 1.4 | 4.5 | 193 |
| Cr | 0.6 | 0.3 | 605 |
| Ti | 0.8 | 1.0 | 865 |
| Sc | 0.6 | 0.9 | 169 |
| Au | 0.7 | 3.9 | 763 |
| Ni | 0.8 | 1.5 | 968 |
| Ge | 0.9 | 0.4 | 691 |
| Zr | 0.6 | 3.1 | 398 |

$^{(a)}$"Apparent alpha" at 538° C. in He after 1 hour on stream.

EXAMPLE 37

The catalysts of Table 2 were used in heptane aromatization reactions which were conducted at 538° C. in a down-flow glass reactor, and the reactor effluents were analyzed directly by on-line gas chromatography. Heptane was introduced into the reactor in a nitrogen stream passing through a vaporizer containing n-heptane at 15°–20° C.

The aromatization reaction of n-heptane at 538° C. and 30 torr in nitrogen was chosen to evaluate and characterize various Pt/ZSM-5 catalysts. In general, Pt/ZSM-5 catalysts fell into three broad classes: (1) acidic, producing low overall yields of aromatics and high yields of $C_3$–$C_4$ hydrocarbons; (2) non-acidic, producing significant amounts of both benzene and toluene together with considerable methane; and (3) non-acidic bimetallic (i.e., metal-modified), characterized by extremely high yields of toluene with low methane formation.

The first class was exemplified by a Pt/H-Ga-ZSM-5 material prepared by ion-exchanging out all sodium ions prior to platinum incorporation. Under the test conditions, $C_5^-$ selectivities, mainly propylene and butenes, were greater than 70% while total aromatic selectivities were less than 20%.

The second class was exemplified by non-acidic Pt/ZSM-5 catalysts prepared from a very high silica/alumina ZSM-5 or from a low aluminum content borsilicate (see Table A).

Aromatic selectivities of the reactions catalyzed by Table 2 compositions and reported in Table A were in the 62–66% range with benzene frequently exceeding the toluene produced. The major $C_5^-$ product formed was methane, which was produced in greater than 30% selectivity at high heptane conversions.

Non-acidic Pt/ZSM-5 catalysts, synthesized in the presence of and containing the following elements: chromium, titanium, scandium, gold, nickel, germanium, or zirconium, also fell into this second category as shown in Table A. Some variations in selectivities were observed (primarily as a function of conversion); however, in no case was the yield of toluene greater than 50–55%. Methane was again the prime light gas produced over these catalysts.

In contrast to these bimetallic catalysts, non-acidic bimetallic Pt/ZSM-5 containing the modifiers: indium, tin, thallium, or lead, exhibited dramatically enhanced toluene selectivities approaching 95% or better (on a mole basis).

The improved aromatization selectivity of these catalysts is due to suppression of hydrogenolysis by platinum, especially methane formation. Reduction in hydrogenolysis selectivity of various metal catalysts by alloying with other metals so as to form more selective mixed metal clusters has been reported in the literature, J. H. Sinfelt, "Bimetallic Catalysts", J. Wiley, New York, 1983; L. Guczi, in Stud. Surf. Sci, Cat., Elsevier, Amsterdam, 1986, vol. 29, p.547; J. Volter, in Stud. Surf. Sci. Cat., Elsevier, Amsterdam, 1986, vol. 27, p.337.

What is claimed is:

1. A process for producing aromatics from dimethylhexanes, said dimethylhexanes contained in a mixture of $C_4$ plus paraffins which mixture also contains an amount of trimethylpentanes comprising contacting said mixture with a catalyst, under dehydrocyclization conditions wherein the catalyst comprises a dehydrogenation metal and a non-acidic microporous crystalline support wherein the support is a material which contains an element selected from the group consisting of tin, thallium, indium and lead and which exhibits the X-ray diffraction pattern of a zeolite; and recovering dehydrocyclization products of said dimethylhexanes and recovering said amount of trimethylpentanes.

2. The process of claim 1, wherein said mixture is an alkylate product produced by addition reactions of at least one paraffin selected from the group of $C_4$–$C_5$ paraffins and $C_3$–$C_5$ olefins.

3. The process of claim 1, wherein the dehydrocyclization conditions include a temperature of from about 400° to about 600° C., pressures from about 0 to about 200 psig; and weight hourly space velocity of from 0.1 to about 10.

4. The process of claim 1, wherein the material exhibits the X-ray pattern of ZSM-5.

5. The process of claim 1, wherein the dehydrogenation metal is platinum.

6. The process of claim 5, wherein the platinum is intrazeolitic.

7. The process of claim 1, wherein said products contain 8 carbon atoms.

8. The process of claim 1, wherein the product contains aromatic compounds.

9. The process of claim 7, wherein the product contains aromatic compounds.

10. The process of claim 1, wherein the microporous crystalline material is characterized by an X-ray diffraction pattern of a zeolite which in its acid form has a constraint index of 1 to 12.

11. A process for increasing the research octane number of an effluent mixture produced by reacting one or more paraffins selected from the group consisting of $C_2$ to $C_5$ paraffins to form an addition product mixture which includes dimethylhexane(s) wherein said process comprises contacting said effluent with a catalyst, under dehydrocyclization conditions, wherein the catalyst comprises dehydrogenation metal and a non-acidic microporous crystalline material and recovering trimethylpentanes and dehydrocyclization products of dimethylhexane.

12. The process of claim 11, wherein the X-ray diffraction pattern is of ZSM-5.

13. The process of claim 11, wherein the microporous crystalline material has an X-ray diffraction pattern of a zeolite and contains tin, indium, thallium or lead.

14. The process of claim 11, wherein the dehydrogenation metal is platinum.

15. The process of claim 12, wherein the dehydrogenation metal is platinum.

16. The process of claim 12, wherein said platinum is intrazeolitic.

17. The process of claim 11, wherein the microporous crystalline material exhibits an X-ray diffraction pattern of a zeolite which in its acidic form has a constraint index of 1 to 12.

18. The process of claim 11, wherein said analogs contain 8 carbon atoms.

19. The process of claim 11, wherein the product contains aromatic compounds.

20. The process of claim 18, wherein the product contains aromatic compounds.

21. The process of claim 1, wherein said element is tin.

22. The process of claim 5, wherein said element is tin.

* * * * *